United States Patent

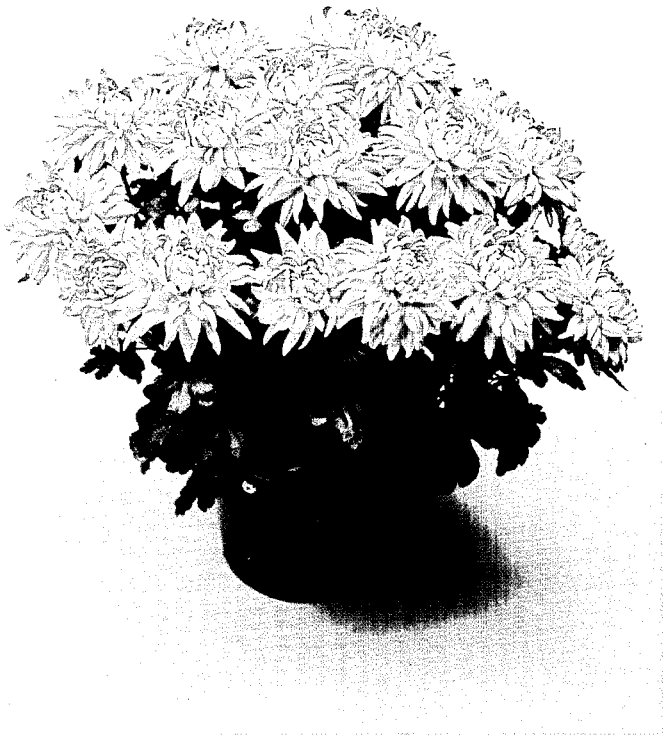
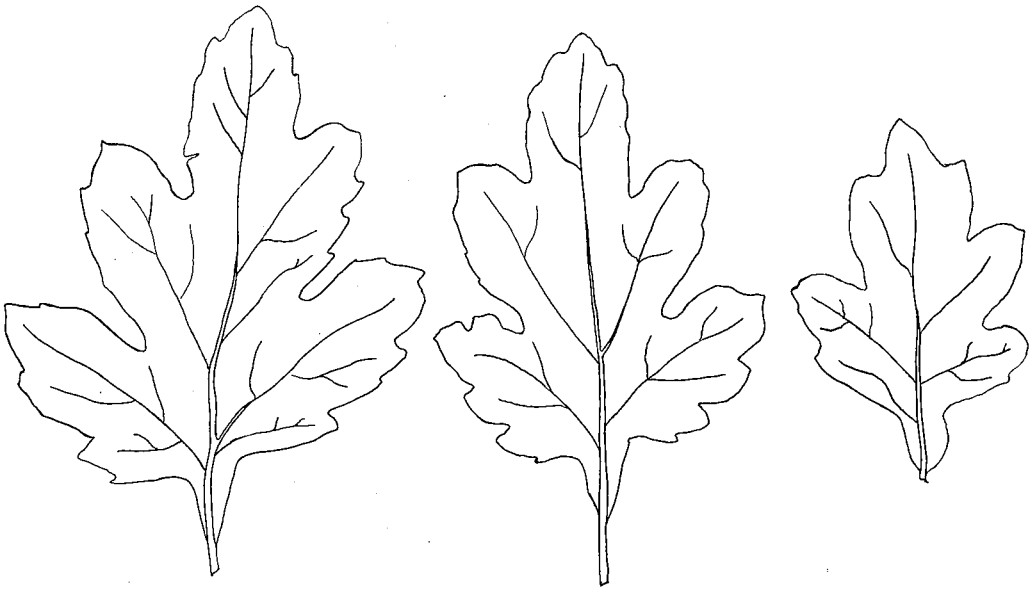

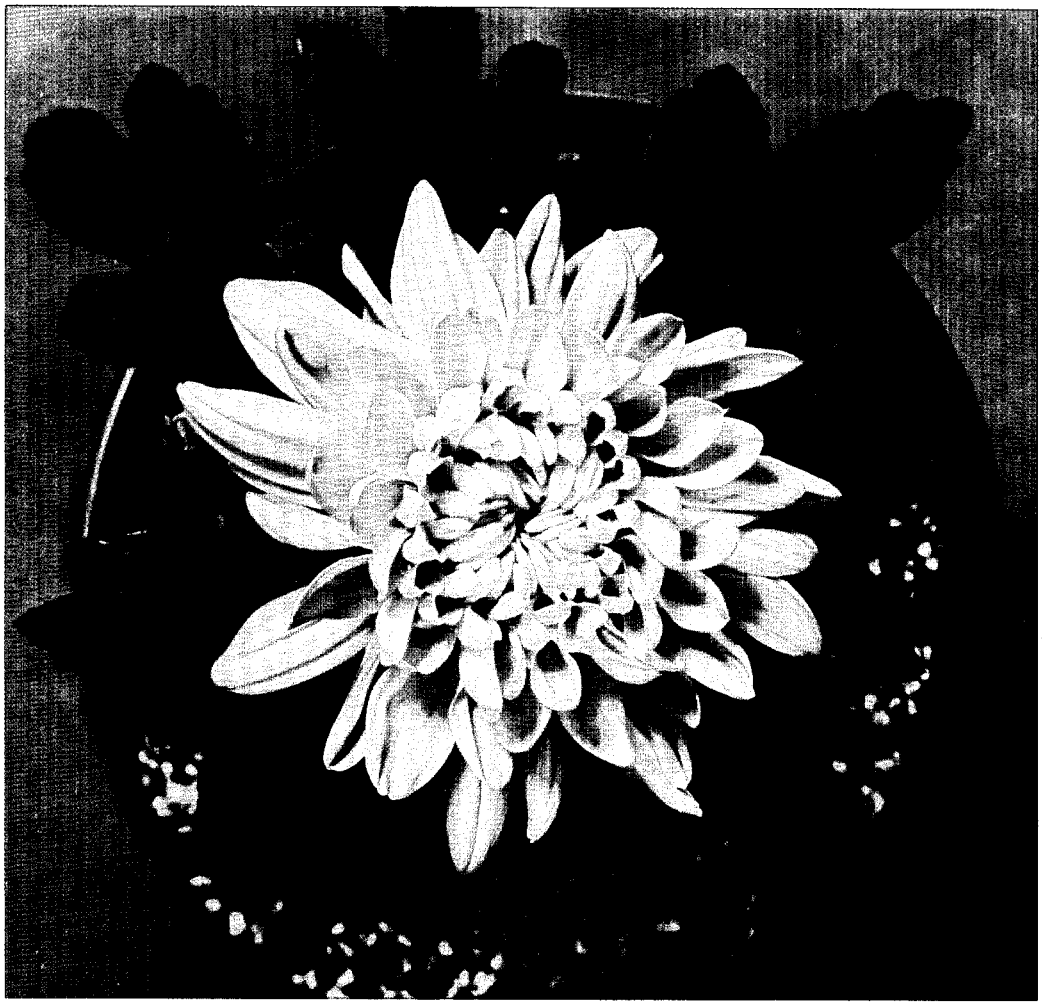
A B C

Plant Pat. 3,832

Patented Mar. 2, 1976

3,832

CHRYSANTHEMUM (MINUTEMAN)

Leonard H. Shoesmith, Westfield, Woking, Surrey, England, assignor to Pan-American Plant Company, West Chicago, Ill.

Filed Nov. 4, 1974, Ser. No. 520,426

Int. Cl. A01h 5/00

U.S. Cl. Plt.—79 1 Claim

ABSTRACT OF THE DISCLOSURE

A new and distinct cultivar of chrysanthemum of the greenhouse pot plant type characterized by the Spanish orange color of the top side and the greyed yellow color on the under side of the florets comprising its semi-incurved flower form the outer petals of which are reflexed, its 9-week response and capability of year around flowering with photo-period control, and its vigorous, terminal, low spreading growth habit.

BACKGROUND OF THE NEW PLANT

My new variety of chrysanthemum was discovered by me among random pollinated seedlings of unidentified parentage growing under glass at West Chicago, Ill., where my breeding efforts are being carried on with the object of developing new and commercially important chrysanthemum varieties. This plant was selected for propagation and test because of its brilliant and unusual color combination and its vigorous growth habit and propagation by means of vegetative cuttings was done by me and under my direction at West Chicago, Ill., to test the plant for its commercial possibilities. Subsequent propagation of this plant at West Chicago, Ill., has demonstrated that its novel characteristics hold true from generation to generation and appear to be firmly fixed.

DESCRIPTION OF THE DRAWING

This new chrysanthemum variety is illustrated by the accompanying photographic drawings on which sheet 1 shows a potted plant display illustrating the general flower form of this variety and includes pen and ink drawings of the leaves of the plant taken at several stages of maturity; and sheet 2 shows a face view of a fully opened flower of this plant, the color rendition of this view being as nearly true as can be had by conventional photographic procedures. The true colors are shown by the hand painted swatches A, B, and C affixed to sheet 2 below the view of the flower, swatch A being the upper side color of the outer florets, swatch B being the upper side color of the inside florets, and swatch C being the color of the reverse side of both outer and inner florets.

DESCRIPTION OF THE NEW PLANT

The following is a detailed description of my new chrysanthemum with color designations according to the Horticultural Colour Chart and the R. H. S. Colour Chart published by The Royal Horticultural Society of London, England, in collaboration with the British Colour Council.

The plant

Origin.—Seedling.
Parentage.—Unidentified.
Classification:
*Botanic.—Chrysanthemum morifolium.*
*Commercial.*—Greenhouse pot plant.
Form.—Perennial herbaceous bush.
Height.—9½ to 10 inches.
Growth.—Terminal; vigorous, low spreading and upright.
Branching.—Normal, with 4 or 5 strong and sturdy breaks when pinched.

Foliage.—Abundant, about 9 leaves low on each stem.
*Leaf Size.*—About 3½ inches long x 2⅛ inches wide.
*Leaf Shape.*—Lobed ovate with a small point on each lobe where the veins appear to be extended.
*Venation.*—Pinnately veined.
*Color.*—Upper side—Ivy Green ooo1060/2. Under side—Leek green ooo85.
*Surface texture.*—Canescent.
*Appearance.*—Glossy.
*Petioles.*—¾ inch long.

The bud

Form.—Almost global.
Size.—About ⅜ inch in diameter and ¼ inch deep.
Opening rate.—Bud opens slowly.
Color.
*When phyllaries first divide.*—Primrose Yellow 601/1.
*When florets begin to unfurl.*—Barium Yellow 503.
Phyllaries.—The outside of the receptacle bears many involucral bracts which stand up and are spear-shaped.
*Color.*—Inside — Lettuce Green 861. Outside—Lettuce Green 861.
*Surface texture.*—Canescent.
Peduncle.—Strong and erect.
*Length.*—¾ inch to 1 5/16 inches.
*Surface texture.*—Canescent.

The flower

Flowering capability.—The plant can be flowered the year around with photoperiod control.
*Response.*—9 week.
*Recommended flowering.*—May to October in the Northern States. March to November in the South.
*Natural season flowering.*—About October 27.
Blooms:
*Flower type.*—Composite and decorative incurve.
*Borne.*—Either singly when disbudded or in multiples of 6 or more when grown as a spray plant.
*Size.*—Large 3½ to 4½ inches in diameter and 1¾ inches in depth.
*Shape.*—Cup shaped when bloom first opens. Central petals remain incurved to form a high center and outer petals spread and become reflexed.
*Florets.*—Number—Numerous. Form: Linear with obtuse apex. Outer petals inversely spooned. Color: Upper side. Outer florets—Spanish orange HCC o10/1, RHS 26 B. Inside florets—Spanish Orange HCC o10; RHS 26 A. Reverse side. Outer florets—Greyed yellow RHS 162B. Inner florets—Greyed yellow RHS 162B. Firmness: Medium. Appearance—Very slight shine. Discoloration—Slight fade.
*Peduncle.*—Sturdy and upright. Length—⅝ inch to 1 inch. Color.—Lavender Green ooo761.
*Persistence.*—Petals persist.
*Fragrance.*—Slight.
*Lasting quality.*—3 weeks on plant. Not recommended for cut flowers.

Reproductive organs

Stamens.—Arrangement—5 synegeneious stamens, connate by their anthers to form a cylinder about the style.
*Filaments.*—⅛ inch long. Color—Light yellow.
*Pollen.*—Yellow in color.
Pistils.—One to each ray floret.
*Style.*—About 3/16 inch long.
*Stigma.*—Uranium Green 63/1.
Ovaries.—Inferior and bicarpellate.

This new chrysanthemum is particularly distinguished by its Spanish orange and greyed yellow coloring, the greyed yellow appearing on the reverse side of the semi-incurved florets comprising the generally globular formation the central area of the bloom; and by the very dark glossy foliage. The vigor and plant habit of this variety is similar to that of the cultivar Delaware and the plant performs as described when flowered as a disbud pot plant from May to October at a latitude of 42° N.

I claim:

1. A new and distinct cultivar of chrysanthemum substantially as herein shown and described, characterized by the Spanish orange and greyed yellow coloration of its large and open blooms of a composite and decorative incurve type, and by its very dark and glossy foliage.

No references cited.

ROBERT E. BAGWILL, Primary Examiner